United States Patent
Goodison et al.

(10) Patent No.: US 9,249,467 B2
(45) Date of Patent: Feb. 2, 2016

(54) BLADDER CANCER DETECTION COMPOSITION, KIT AND ASSOCIATED METHODS

(76) Inventors: Steven Goodison, Jacksonville, FL (US); Charles J. Rosser, Jacksonville, FL (US)

( * ) Notice: Subject to any disclaimer, the term of this patent is extended or adjusted under 35 U.S.C. 154(b) by 0 days.

(21) Appl. No.: 13/617,878

(22) Filed: Sep. 14, 2012

(65) Prior Publication Data
US 2013/0184172 A1 Jul. 18, 2013

Related U.S. Application Data

(60) Provisional application No. 61/535,502, filed on Sep. 16, 2011, provisional application No. 61/557,627, filed on Nov. 9, 2011.

(51) Int. Cl.
*G01N 33/574* (2006.01)
*C12Q 1/00* (2006.01)
*G01N 33/68* (2006.01)
*C12Q 1/68* (2006.01)

(52) U.S. Cl.
CPC ........ C12Q 1/6886 (2013.01); G01N 33/57407 (2013.01); G01N 33/6893 (2013.01); *C12Q 2600/158* (2013.01); *G01N 2800/52* (2013.01); *G01N 2800/7028* (2013.01)

(58) Field of Classification Search
None
See application file for complete search history.

(56) References Cited

U.S. PATENT DOCUMENTS

| 2010/0086932 A1* | 4/2010 | Alcaraz Asensio et al. ...... 435/6 |
| 2010/0184049 A1* | 7/2010 | Goodison et al. ................. 435/6 |
| 2012/0058489 A1 | 3/2012 | Saito et al. |
| 2012/0149043 A1 | 6/2012 | Cohen et al. |

FOREIGN PATENT DOCUMENTS

WO   WO 2011-093927 A1   8/2011

OTHER PUBLICATIONS

Rosser et al. (2013), Multiplex Protein Signature for Detection of Bladder Cancer in Voided Urine Sample., J. Urol. vol. 190(6)., pp. 2257-2262.*
Goodison et al. "Derivation of Cancer Diagnostic and Prognostic Signatures from Gene Expression Data," *Bioanalysis*, vol. 2(5): 855-862, May 2010.
Kaufman et al. "Bladder Cancer," *Lancet*, vol. 374: 239-249, Jun. 10, 2009.
Rosser etal. "Bladder Cancer-Associated Gene Expression Signatures Identified by Profiling of Exfoliated Urothelia," *Cancer Epidemiol. Biomarkers Prev.*, vol. 18(2): 444-453, Feb. 2009.
Trivedi et al. "Commentary: The Roles of Cytologic Analysis of Voided Urine in the Work-up of Asymptomatic Microhematuria," *BMC Urology*, vol. 9: 13, Sep. 10, 2009.
Wagner et al. "Performance of Different Small Sample RNA Amplification Techniques for Hybridization on Affymetrix GeneChips," *Journal of Biotechnology*, vol. 129: 628-634, Feb. 19, 2007.
Shirodkar, S et al., "Potential Markers in the Early Detection of Bladder Cancer," *Current Opinion in Urology*, Sep. 2009, vol. 19, No. 5, p. 488-493.
Urquidi, V. et al., "A Candidate Molecular Biomarker Panel for the Detection of Bladder Cancer," *Cancer Epidemiology Biomarkers Prevention*, 2012, vol. 21, p. 2149-2158.

\* cited by examiner

*Primary Examiner* — Christine J Saoud
*Assistant Examiner* — Jegatheesan Seharaseyon
(74) *Attorney, Agent, or Firm* — Saliwanchik, Lloyd & Eisenschenk

(57) ABSTRACT

Compositions, kits, and methods for the diagnosis, prognosis, and monitoring of bladder cancer in a subject are provided by detecting in a urine sample a combination of biomarkers. In one embodiment of the invention, a nine-biomarker panel consisting of IL-8, MMP9, SDC1, CCL18, SERPINE1, CD44, VEGF-A, CA9, and ANG may be detected. In another embodiment of the invention, a three-biomarker panel consisting of CCL18, CD44, and VEGF-A may be detected. In yet another embodiment of the invention, a nine-biomarker panel consisting of CA9, CCL18, MMP12, TMEM45A, MMP9, SEMA3D, ERBB2, CRH, and MXRA8 may be detected.

4 Claims, 6 Drawing Sheets

BLADDER CANCER DETECTION COMPOSITION, KIT AND ASSOCIATED METHODS

CROSS-REFERENCE TO RELATED APPLICATIONS

The present application claims the benefit of U.S. Provisional Application Ser. No. 61/535,502 filed on Sep. 16, 2011 and U.S. Provisional Application Ser. No. 61/557,627 filed on Nov. 9, 2011, which are hereby incorporated by reference herein in their entirety, and commonly owned.

FIELD OF THE INVENTION

The present invention is directed to compositions, kits, and methods of cancer detection, and, in particular, to such compositions, kits, and methods for detecting bladder cancer, and, most particularly, to such compositions, kits, and methods for detecting bladder cancer non-invasively. In addition, such compositions, kits, and methods are useful as an adjunct to cytological assessments with the use of immunohistochemical procedures.

BACKGROUND OF THE INVENTION

Bladder cancer is among the five most common malignancies worldwide. Bladder cancer cases for 2010 were estimated at 67,160, with deaths estimated at 13,750 in the U.S. alone (A. Jemal et al., *Cancer Statistics, 2010 CA: A Cancer Journal for Clinicians* 60, 277-300, 2010). When detected early, the 5-year survival rate is approximately 94%; thus timely intervention can dramatically increase the probability of patient survival. At present, more than 80% of bladder tumors are non-invasive papillary tumors (pTa or pT1), but the remaining fraction exhibit muscle invasion at the time of diagnosis and have a much less favorable prognosis.

While radical surgery is required for muscle invasive disease, non-muscle invasive tumors can be treated more conservatively by transurethral resection of the tumor, with or without intravesical therapy; however, more than 70% of patients with early-stage disease will have a recurrence during the first two years after diagnosis, making bladder cancer one of the most prevalent of all cancers. If left untreated, these initially non-invasive lesions can progress to being muscle-invasive (F. Millan-Rodriguez et al., *J. Urol.* 164, 680-84, 2000). The recurrence phenomenon of bladder cancer means that patients require strict surveillance at least yearly. For quality of life and positive clinical outcome, the timely detection of disease recurrence is as important as the initial diagnosis.

The current primary diagnostic approach is cystoscopy coupled with voided urine cytology (VUC). Cystoscopy is an uncomfortable, invasive procedure associated with significant cost and possible infection and trauma. VUC remains the method of choice for the non-invasive detection of bladder cancer; yet, while the assay has good specificity, the sensitivity is suboptimal, especially for low-grade and low-stage tumors (D. S. Kaufman et al., *Lancet* 374, 239-49, 2009; D. Trivedi and E. M. Messing, *BMC Urol.* 9, 13, 2009).

A number of diagnostic protein markers for urinalysis have been developed commercially, but single biomarker assays lack adequate power to replace VUC or reduce the need for repeated cystoscopy. This is not surprising, given the redundancy of signaling pathways, the cross-talk between molecular networks, and the oligoclonality of tumors. Embodiments of the present invention provide identification of alternative biomarkers for detection of bladder cancer in non-invasively obtained material which provides a desirable genome-wide analytical strategy.

SUMMARY

Compositions and methods for diagnosing bladder cancer are provided by way of example. The methods may include detecting an overexpression of at least two biomarkers in combination in a body sample, for example, a urine sample, which are known to contain genes and gene products from the bladder lining, that is, the urothelium. The methods distinguish between samples that are indicative of bladder cancer from those that are indicative of a lack of presence of bladder cancer. One method may rely on the detection of preselected biomarkers in combination that are selectively overexpressed in a disease state but not in normal tissue.

The methods can also be used in combination with other diagnostic techniques, invasive or non-invasive, as are known in the art at present or will be developed in future.

Biomarker overexpression can be assessed at the protein or nucleic acid level. In some embodiments, reagents for practicing the methods of the invention are provided, as well as kits comprising the reagents.

The teachings of the present invention improve upon prior experiments of the current inventors showing the feasibility of gene expression profiling of exfoliated urothelia in order to identify bladder cancer-associated gene signatures (C. J. Rosser et al., *Cancer Epidemiol. Biomarkers Prev.* 18(2), 444-53, February 2009). Here the discovery profiling phase was expanded to 92 cases, and selected candidate biomarkers were validated in two independent sets of 81 and 127 urine samples, respectively. Linear amplification of urothelial cell mRNA enabled the profiling of over 47,000 transcripts in minimal samples, and statistical analyses identified a set of 52 ($p<0.001$) differentially expressed genes associated with bladder cancer.

In the validation phase, a selection of 44 target transcripts were monitored in urothelial cells obtained from naturally micturated urine samples using a quantitative PCR or ELISA strategy. A number of individual genes/proteins show promise as biomarkers for bladder cancer detection, and a biomarker panel of a plurality of genes/proteins, for example, exemplary nine- and fourteen-panel compositions and kits, achieved very high discriminatory power. These biomarkers can be incorporated into reliable urinalysis assay formats, thereby leading to robust and accurate, non-invasive tests for the detection of bladder cancer and the surveillance of high-risk patients.

One embodiment of the invention may include detecting a urogenital-related cancer in a subject, the method comprising at least one of detecting a presence of and measuring a level of concentration of biomarkers IL-8, MMP9, SDC1, CCL18, SERPINE1, CD44, VEGF-A, CA9, and ANG in a biological sample from a subject, wherein at least one of the presence of the biomarkers and the level of concentration of the biomarkers is indicative of a presence or absence of cancer in the subject. Another embodiment of the invention may include detecting a three-biomarker panel consisting of CCL18, CD44, and VEGF-A. Yet another embodiment of the invention may include detecting a nine-biomarker panel consisting of CA9, CCL18, MMP12, TMEM45A, MMP9, SEMA3D, ERBB2, CRH, and MXRA8.

BRIEF DESCRIPTION OF DRAWINGS

Embodiments of the invention are described by way of example with reference to the accompanying drawings in which.

DETAILED DESCRIPTION OF EMBODIMENTS OF THE INVENTION

Figure 1A:
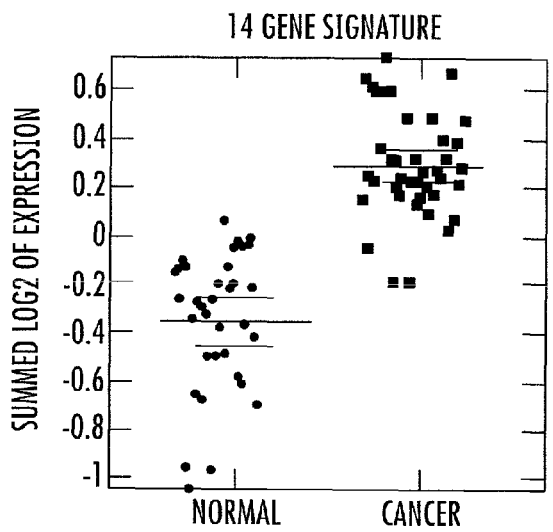
FIG. 1A is a receiver operating characteristic (ROC) curve illustrating the diagnostic accuracy of a 14-gene classifier for bladder cancer.

The present invention will now be described more fully hereinafter with reference to the accompanying drawings, in which embodiments of the invention are shown by way of illustration and example. This invention may, however, be embodied in many forms and should not be construed as limited to the embodiments set forth herein. Rather, these embodiments are provided so that this disclosure will be thorough and complete, and will fully convey the scope of the invention to those skilled in the art. U.S. Patent Application Pub. No. US 2010/0184049 A1 is incorporated by reference herein in its entirety.

Under IRB approval and informed consent, urothelial samples and associated clinical information were prospectively collected from individuals with no previous history of urothelia carcinoma. Patients were undergoing complete hematuria workup, including office cystoscopy and upper tract imaging by computed tomography of the abdomen and pelvis (without and with intravenous contrast). In one study, two different clinical cohorts were analyzed. The first group (test) consisted of 40 subjects with a negative evaluation (i.e., no evidence of cancer), and 52 subjects with a visible bladder tumor detected by upper tract imaging and/or cystoscopy, and which was later proven by evaluation of a biopsy to be urothelial carcinoma. Sampling of exfoliated urothelia for the test group was obtained by injection of 50 ml of saline into the bladder during the time of their office cystoscopy (barbotage) (C. J. Rosser et al., ibid.). The saline solution was substantially immediately aspirated (50 ml) and collected for subsequent analysis.

The second group (validation) comprised 37 subjects with a negative evaluation and 44 cases of confirmed bladder cancer. For this group 30-50 ml of midstream urine was collected in a sterile cup, stored substantially immediately at 4° C., and processed for storage within one hour of collection. Specimens with clearly visible gross hematuria were excluded from analysis.

Urinary creatinine, blood, leukocytes, nitrite, glucose, pH, ketone, and bilirubin were measured for all samples prior to processing using MULTISTIX PRO Reagent Strips (Bayer HealthCare, Elkhart, Ind.). Pertinent information on presentation, histologic grading and staging, therapy, and outcome were recorded. A summary of clinical data is given in Table 1. Each sample was assigned a unique identifying number before immediate laboratory processing. Urothelial cells were pelleted by centrifugation (600×g, 4° C., 5 min), rinsed in PBS, pelleted again, and lysed by direct application of RNeasy lysis buffer (Qiagen, Valencia, Calif.). RNA samples were evaluated quantitatively and qualitatively using an Agilent Bioanalyzer 2000, prior to storage at −80° C.

TABLE 1

Demographic and clinicopathologic characteristics of two study cohorts.

| | Phase I | | Validation | |
|---|---|---|---|---|
| | Noncancer (%) N = 40 | Cancer (%) N = 52 | Noncancer (%) N = 37 | Cancer (%) N = 44 |
| Median Age (range, y) | 69 (30-90) | 68 (36-90) | 69 (19-79) | 67 (47-90) |
| Male/Female ratio | 26:14 | 42:10 | 21:16 | 36:8 |
| Race | | | | |
| White | 30 (75) | 48 (92) | 32 (86) | 40 (91) |
| African American | 7 (18) | 3 (6) | 4 (11) | 3 (7) |
| Other | 3 (7) | 1 (1) | 1 (3) | 1 (2) |
| Suspicious/positive cytology | 0 (0) | 16 (31) | 0 (0) | 12 (27) |
| Clinical stage | | | | |
| Tis | n/a | 3 (6) | n/a | 0 (0) |
| Ta | n/a | 11 (21) | n/a | 9 (20) |
| T1 | n/a | 16 (31) | n/a | 8 (18) |
| T2 | n/a | 22 (42) | n/a | 24 (55) |
| T3 | n/a | 0 (0) | n/a | 3 (7) |
| Grade | | | | |
| 1/2 | n/a | 9 (16) | n/a | 7 (16) |
| 3 | n/a | 43 (84) | n/a | 37 (84) |

Gene expression profiling was performed on Affymetrix Human Genome arrays according to standard protocols (Affymetrix, Santa Clara, Calif.). However, due to the paucity of RNA recovered from the urothelial samples (50-200 ng total RNA), a double amplification protocol was employed (Rosser et al., ibid.; F. Wagner and U. Radelof, *J. Biotechnol.* 129, 628-34, 2007).

Preparation of labeled cRNA was performed according to the Affymetrix Two-Cycle Target Labeling Assay (Affymetrix). Fragmented, biotinylated cRNA was hybridized to Affymetrix Human Genome U133 Plus 2.0 microarrays. Quality control (QC) of each GeneChip experiment included the assessment of the 5':3' ratio. This index reflects not only the original level of RNA integrity but also the accuracy of sample processing (Rosser, ibid.). Any samples that had a 5':3' index <1 were removed from analysis. The 92 cases described herein were those of 106 total cases profiled that passed this criterion. Quantile and dChip normalization was used to generate signal values. The two-sample Welch t-statistics that allows for unequal variances was used to identify genes that were differentially expressed between normal and tumor samples. The p value was used to assess the statistical significance for each gene. The above analyses were conducted using Bioconductor and Analyzelt Tools (http://genomics3.biotech.ufl.edu/Analyzelt/Analyzelt.html). All microarray data obtained in the course of this study are available at GEO XYZ.

To derive a diagnostic optimal multi-gene diagnostic signatures from the microarray data, the LoGo feature selection algorithm was applied (Y. Sun et al., *IEEE Trans. Pattern Anal. Mach. Intell.* 23(9), 1610-26, 2010; Y. Sun and S. Goodison, *Prostate* 69, 1119-27, 2009). To avoid possible overfitting of computational models to training data, the leave-one-out cross validation (LOOCV) method was used to estimate classifier parameters and prediction performance (S. Goodison et al., *Bioanalysis* 2(5), 855-62, May 2010). A receiver operating characteristic (ROC) curve (L. F. Wessels et al., *Bioinformatics* 21, 3755-62, 2005) obtained by varying a decision threshold was used to provide a direct view of how a prediction model performed at different sensitivity and specificity levels. Here, specificity is defined as the probability that a patient who did not have bladder cancer was assigned to the normal group, and the sensitivity is the probability that a patient who had bladder cancer was assigned to the disease group. Scatter plots were created to illustrate relative prediction scores and significance between groups was evaluated using t-tests.

For quantitative PCR analysis, mid-stream urine sample collection and processing for RNA extraction were performed as described above for microarray analysis. Purified RNA samples were evaluated quantitatively and qualitatively using an Agilent Bioanalyzer 2000, prior to storage at −80° C. Complementary DNA was synthesized from 20 to 500 ng of total RNA, depending on availability, using the High Capacity cDNA Reverse Transcriptase Kit (Applied Biosystems, Foster City, Calif.) following the manufacturer's instructions, with random primers in a total reaction volume of 20 µl.

Selection of endogenous reference controls was accomplished by using an aliquot of each sample cDNA in a multiplex PCR preamplification0 reaction of 15 endogenous reference targets: GAPDH; ACTB; B2M; GUSB; HMBS; HPRT1; IPO8; PGK1; POLR2A; PPIA; RPLP0; TBP; TFRC; UBC; YWHAZ. The 15 TaqMan Gene Expression Assays were pooled together at 0.2× final concentration. Subsequently, 12.5 µl of the pooled assay mix (0.2×) was combined with 4 µl of each cDNA sample and 25 µl of the TaqMan® PreAmp Master Mix (2×) in a final volume of 50 µl. Thermal cycling conditions were as follows: initial hold at 95° C. during 10 min and ten preamplification cycles of 15 sec at 95° C. and 4 min at 60° C. The preamplification products were diluted 1:5 with TE buffer prior to singleplex reaction amplification using the TaqMan® Endogenous Control Array (Applied Biosystems), a 384-well micro-fluidic card containing the 15 genes listed above plus 18S RNA. The reactions were performed on a 7900HT Fast Real-Time PCR System (AB). Genes with the least variable expression across all 81 validation samples (UBC; PPIA; PGK1; GAPDH) were identified using GeNorm software (Integromics, Granada, Spain) and subsequently selected for the 48-target custom TLDA build.

Custom array preamplification and amplification reactions were carried out by constructing TaqMan® Low Density Arrays (TLDA) by Applied Biosystems (AB) using pre-designed assays whose probe would span an exon junction. Targets included were: UBC; PPIA; PGK1; GAPDH (4 endogenous controls); BIRC5; TERT; KRT20; CLU; PLAU; CALR; ANG; CA9; SCG3; ATF3; TLR2; AGT; DMBT1; ERBB2; CTNNA1; ATM; FBXO9; CCNE2; NUSAP1; SNAI2; PLOD2; MMP12; IL1RAP; ITGB5; DSC2; APOE; TMEM45A; SYNGR1; MMP10; IL8; VEGFA; CPA1; CCL18; CRH; MCOLN1 SERPINE1 MMP1; MMP9; FGF22; MXRA8; NRG3; SEMA3D; PTX3; RAB1A (44 biomarker targets). A multiplex PCR preamplification reaction was performed using the pooled 48 TaqMan® Gene Expression Assays. Assay reagents at 0.2× final concentration were combined with 7.5 µl of each cDNA sample and 15 µl of the TaqMan PreAmp Master Mix (2×) in a final volume of 30 µl. Thermal cycling conditions were as follows: initial hold at 95° C. during 10 min; fourteen preamplification cycles of 15 sec at 95° C. and 4 min at 60° C. and a final hold at 99.9° C. for 10 min. Ten microliters of undiluted preamplification products was used in the subsequent singleplex amplification reactions, combined with 50 µl of 2× TaqMan® Universal PCR MasterMix (AB) in a final volume of 100 µl, following manufacturer's instructions. One sample of Human Universal Reference Total cDNA (Clontech) was included as a calibrator in each micro-fluidic card. The reactions were run in a 7900HT Fast Real-Time PCR System (AB).

Real-time PCR amplification results were processed with RQ manager (AB) and StatMiner (Integromics) software packages. The baseline correction was manually checked for each target, and the Ct threshold was set to 0.2 for every target across all plates. One sample that amplified <10% of the 48 targets was removed from the analysis, and one target (PTX3) was removed from all subsequent analyses because amplification curve analysis revealed amplification of non-specific products. Delta-Delta CT values were calculated using a geometric average of the four endogenous reference targets (UBC, PPIA, PGK1, and GAPDH) as normalizer and Human Universal Reference Total cDNA (Clontech) as the calibrator. Genes deemed to be differentially expressed between bladder cancer and non-cancer samples were determined by t-test comparison (p<0.01).

Derivation of optimal diagnostic molecular signatures was accomplished by using L1-regularized logistic regression to establish a prediction model, i.e., to predict the actual status of a given sample as cancer or control. Details of the strategy, optimal solution parameters, and application of a fast implementation approach for L1 regularized learning algorithms will be presented in the following. Due to the small sample size, the leave-one-out cross validation (LOOCV) method was adopted to estimate the prediction performance (Wessels et al., ibid.). In each iteration, one sample was held out for test, and the remaining samples were used for training. The regularization parameter λ was first estimated through ten-fold cross validation using the training data, and then a predictive model was trained using the estimated parameter and blindly applied to the held-out sample.

The experiment was repeated until all samples had been tested. An ROC curve was then plotted to visualize how a prediction model performed at different sensitivity and specificity levels, and the area under receiver operating characteristic curves (AUC) was reported. To verify the data, a permutation test was also performed to estimate the p value of predictive performance. The permutation test was repeated 1000 times. In each iteration, the class labels were randomly shuffled, the above-described experimental protocol was executed, and the area under the resulting ROC curve was recorded. The p value was computed as the occurrence frequencies of the iterations where the resulting AUCs outperformed that obtained using the original class labels. A p value <0.01 was considered to be statistically significant. Statistical analyses were performed by SPSS 13.0, and by MedCalc version 8.0 (MedCalc Software, Mariakerke, Belgium).

Gene expression profiling was accomplished by isolating urothelial cell samples from the urine of 92 patients for molecular profile analysis (test cohort). Of these cases, 52 had biopsy confirmed, early-stage disease (stages Ta, T1 or T2) urothelial carcinoma, and 40 cases had no evidence of cancer. Patient cohort characteristics are summarized in Table 1. The amount of RNA recovered from the urothelial cell samples ranged from 20 to 250 ng of total RNA; so a two-cycle amplification strategy was employed in order to generate sufficient labeled cRNA for hybridization to Affymetrix U133 Plus 2.0 arrays, enabling analysis of over 47,000 transcripts. Data analysis identified a 447-gene set that had expression patterns associated with disease status (p value ≤0.01), with 52 genes having a p value ≤0.001 (see Table 2). Among the top-ranked (≤0.0001), overexpressed transcripts associated with bladder cancer were MMP12 and MMP10, members of the metalloproteinase family of tissue remodeling enzymes.

TABLE 2

52 Genes having expression patterns associated with disease status and having a p value ≤ 0.001.

| Prob_ID | Entrez Gene ID | Gene_Name | T-test-p value |
|---|---|---|---|
| 204580_at | 4321 | MMP12 | 0 |
| 207558_s_at | 5308 | PITX2 | 0 |
| 201291_s_at | 7153 | TOP2A | 0.0001 |
| 226344_at | 84460 | ZMAT1 | 0.0001 |
| 205680_at | 4319 | MMP10 | 0.0001 |
| 233862_at | — | — | 0.0001 |
| 231706_s_at | 2128 | EVX1 | 0.0001 |
| 228415_at | — | — | 0.0002 |
| 232222_at | 400653 | C18orf49 | 0.0002 |
| 212236_x_at | 3872 | KRT17 | 0.0002 |
| 241935_at | 134549 | SHROOM1 | 0.0003 |
| 214472_at | 8351 | HIST1H3D | 0.0003 |
| 203294_s_at | 3998 | LMAN1 | 0.0003 |
| 226950_at | 94 | ACVRL1 | 0.0003 |
| 242414_at | 23475 | QPRT | 0.0003 |
| 211506_s_at | 3576 | IL8 | 0.0004 |
| 218039_at | 51203 | NUSAP1 | 0.0004 |
| 229693_at | 388335 | LOC388335 | 0.0004 |
| 1570352_at | 472 | ATM | 0.0004 |
| 222326_at | — | — | 0.0004 |
| 232690_at | — | — | 0.0005 |
| 223816_at | 57864 | SLC46A2 | 0.0005 |
| 218279_s_at | 8337 | HIST2H2AA3 | 0.0005 |
| 240065_at | 153643 | FAM81B | 0.0005 |
| 232081_at | — | — | 0.0005 |
| 209942_x_at | 4102 | MAGEA3 | 0.0005 |

TABLE 2-continued

52 Genes having expression patterns associated with disease status and having a p value ≤ 0.001.

| Prob_ID | Entrez Gene ID | Gene_Name | T-test-p value |
|---|---|---|---|
| 221828_s_at | 89853 | FAM125B | 0.0005 |
| 243282_at | 54520 | CCDC93 | 0.0005 |
| 214456_x_at | 6288 | SAA1 | 0.0006 |
| 210513_s_at | 7422 | VEGFA | 0.0006 |
| 236504_x_at | 347744 | C6orf52 | 0.0006 |
| 236193_at | 8347 | HIST1H2BC | 0.0006 |
| 213418_at | 3310 | HSPA6 | 0.0006 |
| 228044_at | 387923 | SERP2 | 0.0006 |
| 238773_at | 196074 | METT5D1 | 0.0006 |
| 220856_x_at | — | — | 0.0006 |
| 205615_at | 1357 | CPA1 | 0.0007 |
| 205034_at | 9134 | CCNE2 | 0.0007 |
| 215424_s_at | 22938 | SNW1 | 0.0007 |
| 229321_s_at | — | — | 0.0007 |
| 220724_at | 80157 | FLJ21511 | 0.0007 |
| 117_at | 3310 | HSPA6 | 0.0008 |
| 226448_at | 375061 | FAM89A | 0.0008 |
| 209072_at | 4155 | MBP | 0.0009 |
| 229266_at | 284033 | LOC284033 | 0.0009 |
| 32128_at | 6362 | CCL18 | 0.001 |
| 207494_s_at | 7629 | ZNF76 | 0.001 |
| 225191_at | 1153 | CIRBP | 0.001 |
| 209773_s_at | 6241 | RRM2 | 0.001 |
| 238472_at | 26268 | FBXO9 | 0.001 |
| 243726_at | — | — | 0.001 |
| 222598_s_at | 730427 /// 89797 | LOC730427 | 0.001 |

From a list of genes ranked only by p value, it is not clear which are the most relevant to the classification task at hand, in this case, stratifying cancer versus non-cancer cases. Once p values become increasingly small, one cannot be sure that the top-ranked genes are the most important individually, or that they would perform optimally as a multiple biomarker signature for bladder cancer classification. In order to identify the most accurate diagnostic signatures from the microarray data, a feature selection algorithm was applied that had previously been derived and applied to the derivation of optimal disease classifiers in breast and prostate cancer (C. J. Rosser et al., ibid.; Y. Sun and S. Goodison, ibid.; S. Goodison et al., ibid.; Y. Sun et al., 2007, ibid.). The algorithm performs multivariate data analyses on high-dimensional data without making any assumptions about the underlying data distribution. This approach identified a 43-gene model (Table 3) that performed best in predicting class label, achieving an area-under-ROC curve of 0.821, during leave-one-out cross validation. This modeling aided the selection of genes for orthologous technique validation.

TABLE 3

A 43-gene model for predicting class label.

| Prob_ID | Entrez Gene | Gene_Name | Correlation | t-test p value |
|---|---|---|---|---|
| 200650_s_at | 3939 | LDHA | 0.3146 | 0.0023 |
| 202620_s_at | 5352 | PLOD2 | 0.289 | 0.0052 |
| 204287_at | 9145 | SYNGR1 | −0.2944 | 0.0044 |
| 204580_at | 4321 | MMP12 | 0.4269 | 0 |
| 205034_at | 9134 | CCNE2 | 0.3478 | 0.0007 |
| 206197_at | 8382 | NME5 | −0.3128 | 0.0024 |
| 212188_at | 115207 | KCTD12 | 0.3263 | 0.0015 |
| 212884_x_at | 348 | APOE | 0.3108 | 0.0026 |
| 213139_at | 6591 | SNAI2 | 0.2948 | 0.0043 |
| 215283_at | 400642 | LOC400642 | −0.2745 | 0.0081 |
| 216769_x_at | — | — | −0.3006 | 0.0036 |
| 218039_at | 51203 | NUSAP1 | 0.3629 | 0.0004 |
| 218279_s_at | 8337 | HIST2H2AA3 | 0.3574 | 0.0005 |

TABLE 3-continued

A 43-gene model for predicting class label.

| Prob_ID | Entrez Gene | Gene_Name | Correlation | t-test p value |
|---|---|---|---|---|
| 219368_at | 4674 | NAP1L2 | −0.2805 | 0.0068 |
| 219410_at | 55076 | TMEM45A | 0.3023 | 0.0034 |
| 220390_at | 79841 | AGBL2 | −0.2991 | 0.0038 |
| 220856_x_at | — | — | 0.3492 | 0.0006 |
| 222326_at | — | — | 0.3586 | 0.0004 |
| 224834_at | 92181 | UBTD2 | 0.2844 | 0.006 |
| 225100_at | 200933 | FBXO45 | 0.2779 | 0.0073 |
| 225722_at | — | — | −0.2905 | 0.005 |
| 226344_at | 84460 | ZMAT1 | −0.3929 | 0.0001 |
| 226448_at | 375061 | FAM89A | 0.3441 | 0.0008 |
| 226817_at | 1824 | DSC2 | 0.3286 | 0.0014 |
| 227919_at | 652995 | UCA1 | 0.2831 | 0.0062 |
| 228033_at | 144455 | E2F7 | 0.3016 | 0.0035 |
| 228415_at | — | — | 0.3787 | 0.0002 |
| 228825_at | 22949 | LTB4DH | −0.2967 | 0.0041 |
| 232530_at | 5337 | PLD1 | 0.3092 | 0.0027 |
| 236635_at | 63934 | ZNF667 | −0.3207 | 0.0018 |
| 236879_at | — | — | 0.3347 | 0.0011 |
| 238360_s_at | — | — | 0.283 | 0.0063 |
| 238472_at | 26268 | FBXO9 | −0.3366 | 0.001 |
| 238773_at | 196074 | METT5D1 | 0.35 | 0.0006 |
| 239466_at | 344595 | LOC344595 | −0.2972 | 0.004 |
| 239926_at | — | — | −0.2904 | 0.005 |
| 241092_at | — | — | 0.3095 | 0.0027 |
| 241438_at | — | — | 0.3184 | 0.002 |
| 241726_at | — | — | 0.2822 | 0.0064 |
| 242292_at | 653687 /// 729488 | CXorf50B | −0.2705 | 0.0091 |
| 242414_at | 23475 | QPRT | −0.3658 | 0.0003 |
| 244804_at | 8878 | SQSTM1 | 0.2933 | 0.0045 |
| 1562468_at | — | — | 0.3322 | 0.0012 |

In order to validate and refine the bladder cancer diagnostic molecular signature, a selected panel of candidate biomarkers was tested in an independent, validation sample set of naturally voided urine samples, comprising 37 non-cancer controls and 44 cancer cases (Table 1). Target transcripts were measured in urothelial cell RNA samples using quantitative real-time RT-PCR. TaqMan® Low Density Arrays (TLDA) were constructed to include 44 candidate biomarker targets plus 4 selected endogenous controls selected by screening the level of 15 commonly used endogenous controls in the full cohort of samples (described above and below). Biomarker targets were selected primarily from the p-value ranking and molecular signature models described above, but several putative biomarkers were also included from the literature (TERT, KRT20, CLU, PLAU, CALR, CA9, ANG). When other selection criteria were equal, genes were selected that encode integral membrane proteins or secreted proteins, because these classes hold particular potential for development as biomarkers for urinalysis. An exemplary set of selected targets is listed in Table 4, although these are not intended as limiting, and one of skill in the art will appreciate that other gene combinations could be envisioned.

TABLE 4

Expression data for targets included in the TLDA Arrays

| Gene Symbol | Gene Name | Gene ID | AB Assay ID | t-test p value | Fold Change (T/N) |
|---|---|---|---|---|---|
| CA9 | carbonic anhydrase IX | 768 | Hs00154208_m1 | 0.00000001 | 131.63 |
| MMP12 | matrix metallopeptidase 12 | 4321 | Hs00899662_m1 | 0.00000092 | 44.39 |
| CCL18 | chemokine (c-c motif) ligand 18 | 6362 | Hs00268113_m1 | 0.00000460 | 22.03 |
| MMP10 | matrix metallopeptidase 10 | 4319 | Hs00233987_m1 | 0.00004356 | 31.75 |
| TMEM45A | transmembrane protein 45A | 55076 | Hs01046616_m1 | 0.00008920 | 22.43 |
| ANG | angiogenin, ribonuclease, RNase A family, 5 | 283 | Hs01590076_m1 | 0.00050597 | 0.10 |
| SNAI2 | snail homolog 2 (Drosophila) | 6591 | Hs00161904_m1 | 0.00129367 | 8.56 |
| MMP1 | matrix metallopeptidase 1 | 4312 | Hs00233958_m1 | 0.00130198 | 12.77 |
| SERPINE1 | serpin peptidase inhibitor, clade E, member 1 | 5054 | Hs01126606_m1 | 0.00276715 | 6.74 |
| MXRA8 | matrix-remodeling-associated protein 8 | 54587 | Hs00260584_m1 | 0.00352499 | 6.19 |
| MMP9 | matrix metallopeptidase 9 | 4318 | Hs00234579_m1 | 0.00369514 | 5.32 |
| CCNE2 | cyclin E2 | 9134 | Hs00372959_m1 | 0.01295262 | 5.50 |
| BIRC5 | baculoviral IAP repeat containing 5 | 332 | Hs03043576_m1 | 0.01811106 | 5.79 |
| SEMA3D | semaphorin-3D | 223117 | Hs00380877_m1 | 0.02745466 | 4.30 |
| PLAU | plasminogen activator, urokinase | 5328 | Hs00170182_m1 | 0.05165301 | 2.71 |
| SYNGR1 | synaptogyrin 1 | 9145 | Hs00377475_m1 | 0.07291574 | 0.35 |
| SCG3 | secretogranin III | 29106 | Hs00203076_m1 | 0.07437048 | 4.19 |
| NUSAP1 | nucleolar and spindle associated protein 1 | 51203 | Hs00251213_m1 | 0.09570886 | 2.68 |
| CRH | corticotropin releasing hormone | 1392 | Hs00174941_m1 | 0.10892472 | 4.43 |
| TERT | telomerase reverse transcriptase | 7015 | Hs00972649_m1 | 0.10971281 | 4.30 |
| DMBT1 | deleted in malignant brain tumors 1 | 1755 | Hs00244838_m1 | 0.13055893 | 0.23 |
| IL1RAP | interleukin 1 receptor accessory protein | 3556 | Hs00895050_m1 | 0.13249845 | 2.28 |
| NRG3 | neuregulin 3 | 10718 | Hs02385273_m1 | 0.19498374 | 0.36 |
| RAB1A | RAB1A, member RAS oncogene family | 5861 | Hs00366513_m1 | 0.21131502 | 0.63 |
| AGT | angiotensinogen | 183 | Hs00174854_m1 | 0.25373123 | 0.44 |
| PLOD2 | procollagen-lysine, 2-oxoglutarate 5-dioxygenase 2 | 5352 | Hs00168688_m1 | 0.25400609 | 2.15 |
| MCOLN1 | mucolipin 1 | 57192 | Hs01100653_m1 | 0.26029049 | 1.97 |
| FBXO9 | f-box protein 9 | 26268 | Hs00938175_m1 | 0.28712710 | 0.57 |
| IL8 | interleukin 8 | 3576 | Hs00174103_m1 | 0.30782081 | 2.44 |
| CTNNA1 | catenin (cadherin-associated protein), alpha 1, 102 kDa | 1495 | Hs00426996_m1 | 0.31868507 | 0.64 |
| CLU | clusterin | 1191 | Hs00971651_m1 | 0.34720533 | 0.61 |
| ATM | ataxia telangiectasia mutated | 472 | Hs01112307_m1 | 0.40618794 | 1.63 |
| VEGFA | vascular endothelial growth factor A | 7422 | Hs00900055_m1 | 0.59002576 | 1.37 |
| CALR | calreticulin | 811 | Hs00189032_m1 | 0.59909855 | 1.34 |
| DSC2 | desmocollin 2 | 1824 | Hs00245200_m1 | 0.61344566 | 0.76 |

TABLE 4-continued

Expression data for targets included in the TLDA Arrays

| Gene Symbol | Gene Name | Gene ID | AB Assay ID | t-test p value | Fold Change (T/N) |
|---|---|---|---|---|---|
| FGF22 | fibroblast growth factor 22 | 27006 | Hs00221001_m1 | 0.62329020 | 1.32 |
| CPA1 | carboxypeptidase A1 (pancreatic) | 1357 | Hs01056157_m1 | 0.64988150 | 0.70 |
| APOE | apolipoprotein E | 348 | Hs00171168_m1 | 0.67418489 | 1.21 |
| ATF3 | activating transcription factor 3 | 467 | Hs00231069_m1 | 0.71139279 | 0.84 |
| ERBB2 | v-erb-b2 erythroblastic leukemia viral oncogene homolog 2 | 2064 | Hs01001582_m1 | 0.77449803 | 1.19 |
| KRT20 | keratin 20 | 54474 | Hs00300643_m1 | 0.81619326 | 1.20 |
| TLR2 | toll-like receptor 2 | 7097 | Hs00152932_m1 | 0.83787755 | 1.13 |
| ITGB5 | integrin, beta 5 | 3693 | Hs00609896_m1 | 0.97745179 | 0.99 |
| PTX3 * | pentraxin 3, long | 5806 | Hs01073991_m1 | ND | ND |
| UBC | ubiquitin C | 7316 | Hs00824723_m1 | Endog. Control | NA |
| PPIA | peptidylprolyl isomerase A | 5478 | Hs99999904_m1 | Endog. Control | NA |
| PGK1 | phosphoglycerate kinase 1 | 5230 | Hs99999906_m1 | Endog. Control | NA |
| GAPDH | glyceraldehyde-3-phosphate dehydrogenase | 2597 | Hs99999905_m1 | Endog. Control | NA |

* PTX3-Hs01073991_m1 was excluded from the analysis. Produced non-specific amplification.

Figure 1B:
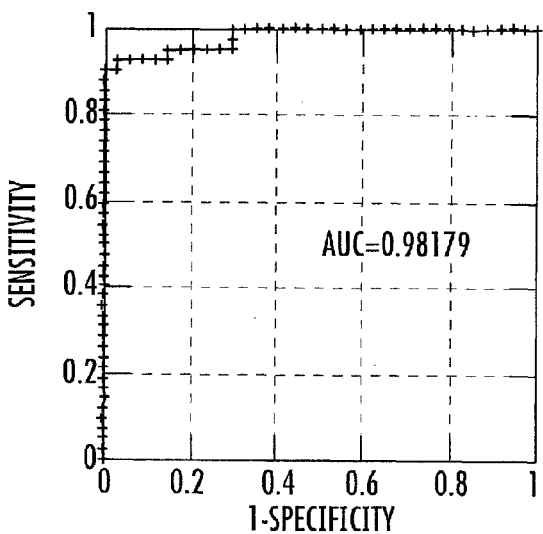
FIG. 1B is an expression distribution of the 14-gene signature on cancer and non-cancer groups.
Figure 1C:
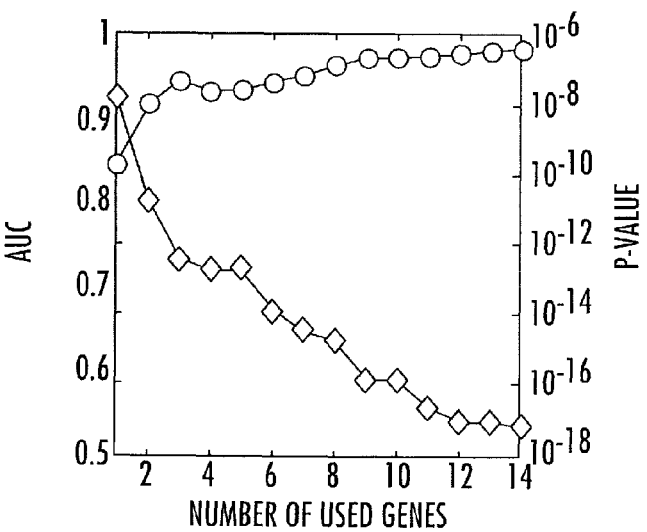
FIG. 1C shows the variation of p values and area under receiver (AUC) operating characteristic curve (AUC) values as a function of the number of genes included in a prediction model.

Differential expression values were calculated by normalization using the reference targets (UBC, PPIA, PGK1, and GAPDH) and Human Universal Reference Total cDNA (Clontech) as the calibrator on each plate. Eleven of the tested genes (Table 4) were revealed to be differentially expressed between bladder cancer and non-cancer samples (p<0.01), with the top five ranked genes having p values <0.001. L1-regularized logistic regression was then used to derive a prediction model, i.e., to identify the molecular signature that could best predict the status of a given sample as cancer or control. ROC curves were plotted to visualize how each prediction model performed at different sensitivity and specificity levels. The optimal signature derived from the 47-target TLDA analysis was composed of 14 genes, as shown in Table 5, from which can be observed that some genes (e.g., DMBT1 and ERBB2) have large p values and thus may not be valuable when evaluated individually, but these targets can provide critical information when combined with a panel of biomarkers. A scatter plot of signature performance showed a significant (p value <0.0001) spread of values between cancer and non-cancer cases (FIG. 1A), and the ROC curve revealed very high sensitivity and specificity values (FIG. 1B). At a sensitivity of up to 90%, the 14-gene signature achieved a specificity of 100%. The area under the ROC curve (AUC) was 0.982. By plotting the variation of signature p values against AUC values, it was revealed that the 9 top-ranked genes contributed most to the 14-gene signature performance; however, the addition of more genes creates a signature more robust against errors (FIG. 1C).

TABLE 5

A 14-gene diagnostic signature for the detection of bladder cancer.

| Gene Symbol | Gene ID | Gene Name | Average Weight* | p value** |
|---|---|---|---|---|
| CA9 | 768 | carbonic anhydrase IX | 0.18 | 1.9e-8 |
| CCL18 | 6362 | chemokine (C-C motif) ligand 18 | 0.16 | 1.3e-5 |
| DMBT1 | 1755 | deleted in malignant brain tumors 1 | −0.09 | 0.14 |
| ANG | 283 | angiogenin, ribonuclease, RNase A family, 5 | −0.08 | 5.0e-3 |
| ERBB2 | 2064 | v-erb-b2 erythroblastic leukemia viral oncogene homolog 2 | 0.08 | 0.57 |
| TMEM45A | 55076 | transmembrane protein 45A | 0.06 | 2.0e-3 |
| SYNGR1 | 9145 | synaptogyrin 1 | −0.06 | 0.12 |
| MMP9 | 4318 | matrix metallopeptidase 9 | 0.05 | 6.2e-3 |
| RAB1A | 5861 | RAB1A, member RAS oncogene family | −0.05 | 0.15 |
| SEMA3D | 223117 | semaphorin 3D | 0.05 | 0.03 |
| DSC2 | 1824 | desmocollin 2 | −0.04 | 0.60 |
| MXRA8 | 54587 | matrix-remodelling associated 8 | 0.02 | 7.4e-3 |
| VEGFA | 7422 | vascular endothelial growth factor A | −0.02 | 0.67 |
| AGT | 183 | angiotensinogen | −0.01 | 0.30 |

*Genes sorted in descending order of average prediction weight. Negative prefix denotes a gene down-regulated in cancer cases.
**p value of each gene obtained by a Student's t-test comparing the distribution of gene expression levels in cancer versus non-cancer case samples.

Figure 2A:
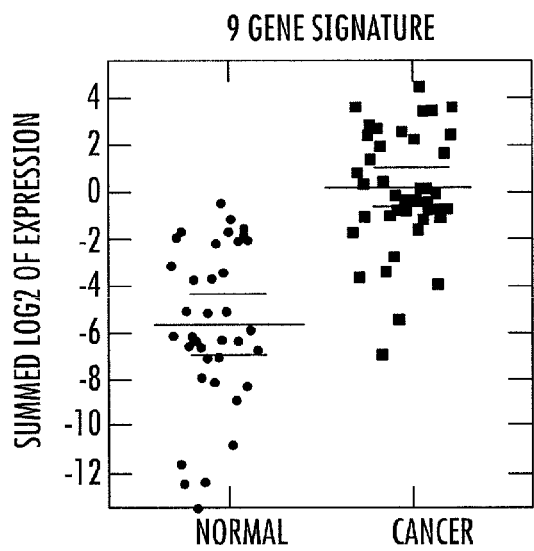
FIG. 2A is a ROC curve illustrating the diagnostic accuracy of a 9-gene classifier for bladder cancer, which comprised only up-regulated genes.
Figure 2B:
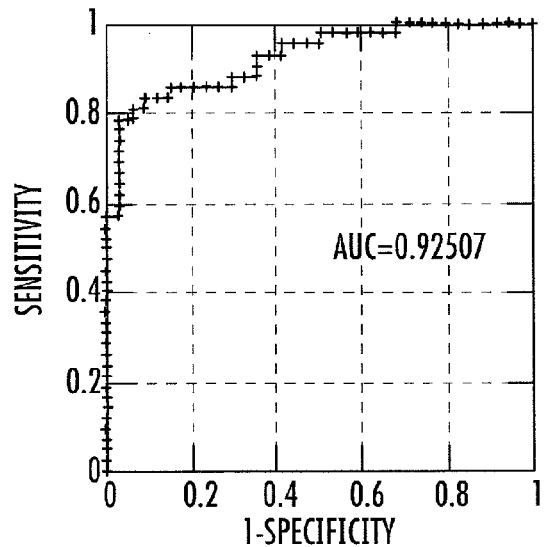
FIG. 2B is an expression distribution of the 9-gene signature on cancer and non-cancer sample groups.
Figure 2C:
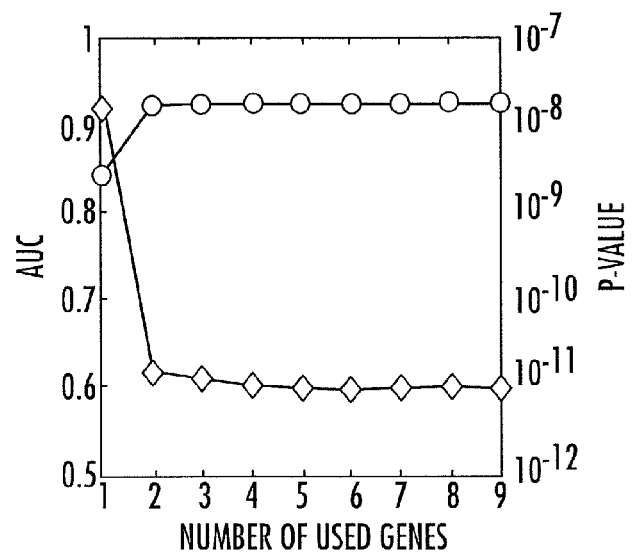
FIG. 2C shows the variation of p values and AUC values with respect to the number of genes included in a prediction model.

The optimal 14-gene model was composed of 7 gene transcripts that were up-regulated in tumor specimens and 7 that were down-regulated. Considering the development of potential biomarker assays, in which up-regulated genes are perhaps more applicable for accurate detection, the performance of signatures derived from the PCR data that were composed of only up-regulated genes was calculated using a constrained L1 regularized logistic regression model, as shown in the data in the following. Considering the limited selection, a 9-gene signature (Table 6) performed very well, achieving an AUC of 0.925 (FIGS. 2A and 2B). At a sensitivity of 80%, the 9-gene signature achieved 98% specificity. Plotting the p-value variation and AUC values revealed that the top 2 ranked genes contributed most to the 9-gene signature (FIG. 2C).

TABLE 6

A 9-gene diagnostic signature for the detection
of bladder cancer. Up-regulated in cancer

| Gene Symbol | Gene ID | Gene Name | Average weight* | p value** |
|---|---|---|---|---|
| CA9 | 768 | carbonic anhydrase IX | 0.48 | 2e−9 |
| CCL18 | 6362 | chemokine (C-C motif) ligand 18 | 0.40 | 1e−5 |
| MMP12 | 4321 | matrix metallopeptidase 12 | 0.075 | 2e−6 |
| TMEM45A | 55076 | transmembrane protein 45A | 0.032 | 0.0002 |
| MMP9 | 4318 | matrix metallopeptidase 9 | 0.0086 | 0.0062 |
| SEMA3D | 223117 | semaphorin 3D | 0.0017 | 0.0301 |
| ERBB2 | 2064 | v-erb-b2 erythroblastic leukemia viral oncogene homolog 2 | 0.0006 | 0.5663 |
| CRH | 1392 | corticotropin releasing hormone | 0.0005 | 0.1853 |
| MXRA8 | 54587 | matrix-remodelling associated 8 | 0.0003 | 0.0074 |

*Genes sorted in descending order of average prediction weight.
**p value of each gene obtained by a Student's t-test comparing the distribution of gene expression levels in cancer versus non-cancer case samples.

A discriminant analysis was performed to assess the prediction value of gene signatures for the diagnosis of bladder cancer. Specifically, L1-regularized logistic regression was used to establish a prediction model due to its ability to handle high-dimensional data (A. Y. Ng, *Proc. 21st Intl. Conf. on Machine Learning*, pp 78-86, 2004). Before the comparative analysis, the individual signal intensity values obtained from the TLDA probes are log transformed using 2 as the base, and normalized between all individual samples included in the study. Given samples and gene probes, the gene expression profile of the -th sample and the corresponding clinical status are denoted (−1 for non-cancer and 1 for cancer). L1-regularized logistic regression seeks an optimal solution to solve the following optimization problem:

$$\min_{w,b} \frac{1}{N} \sum_{n=1}^{N} \log(1 + \exp(-y_n(wx_n - b))) + \lambda \|w\|_1$$

where $\lambda$ is a regulation parameter that controls the sparseness of the solution, $w=[w_1, w_2, \ldots, w_j]$ is the prediction weight vector, and b is the decision threshold. The regulation parameter $\lambda$ was tuned with a cross-validation method to described in the following. The magnitude of each element of w can be interpreted as the predictive value of the corresponding gene. In this analysis, the samples were organized so that a positive weight indicates up-regulation of the corresponding gene and a negative weight for a down-regulation gene. After the prediction model was constructed, given a new gene expression profile x, the prediction score was computed as w*x that indicates the prognostic outcome of bladder cancer. The optimal threshold b* determines the decision boundary between normal and cancer patient profiles. When evaluating the performance of a prediction model, the receiver operating characteristic (ROC) curve is often used and can be obtained by varying the threshold b to yield different specificity and sensitivity levels.

In order to evaluate the predictive power of up-regulated genes, the following constrained form of logistic regression was used:

$$\min_{w \geq 0, b} \frac{1}{N} \sum_{n=1}^{N} \log(1 + \exp(-y_n(w^T x_n - b))) + \lambda \|w\|_1$$

The two optimization problems can be easily solved using the method described in Y. Cai et al. (*Proc. 10th SIAM Intl. Conf. on Data Mining*, pp 862-71. 2010).

Figure 3:
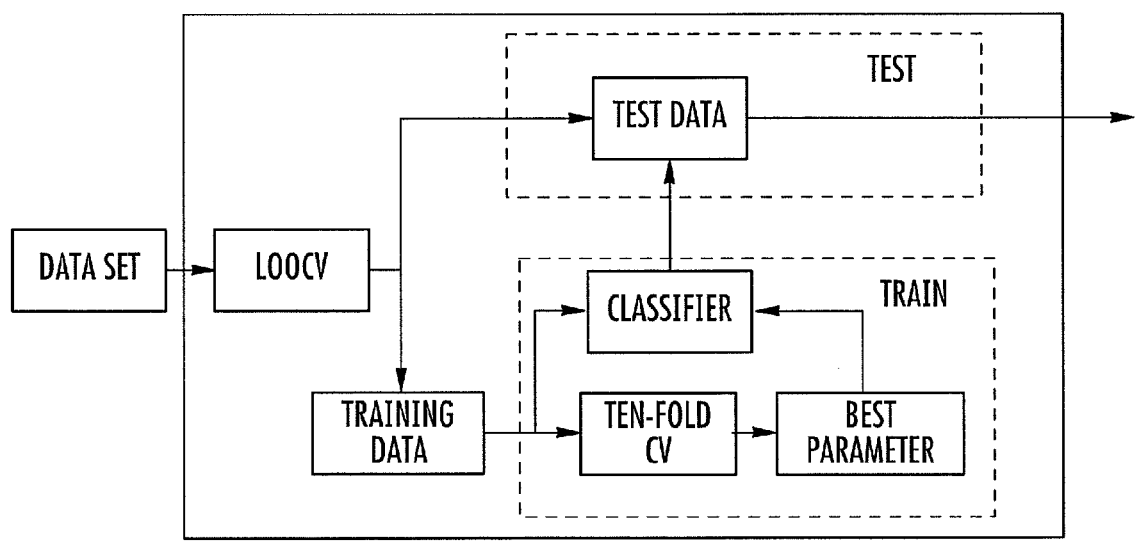
FIG. 3 is a flowchart of an exemplary "leave-one-out cross-validation" (LOOCV) procedure.

Due to the small sample size, the leave-one-out cross validation (LOOCV) method was adopted to estimate the prediction performance. In each iteration, one sample was held out for test, and the remaining samples were used for training. The regularization parameter $\lambda$ was first estimated through ten-fold cross validation using the training data, and then a predictive model was trained using the estimated parameter and blindly applied to the held-out sample. The experiment was repeated until all samples had been tested. Test samples were not involved in any stage of training process (see FIG. 3 for details). An ROC curve was then plotted to visualize how a prediction model performed at different sensitivity and specificity levels, and the area under receiver operating characteristic curves (AUC) was reported.

The prediction weight vector learned in each iteration was recorded and normalized so that:

$$\Sigma_j |w_j| = 1$$

After the entire LOOCV procedure was finished, the average weights of individual genes were computed and sorted in a descending order. By using both up- and down-regulated genes, 14 genes were found to have significant prediction strength defined as $$|w_j| > 0.01$$

By using up-regulated genes, only 4 genes were found to have $$|w_j| > 0.01$$

and 9 genes have non-zero weights. All the 9 genes were thus recorded, although it turned out that only the first 2 genes played a significant role in the decision making.

With a small data size, it is possible that the outcomes of a prediction model are due to some random confounding factors of no interest to investigators. Thus a permutation test was performed to estimate the p value of predictive performance. For computational reasons herein, the permutation test was repeated 1000 times. In each iteration, the class labels were randomly shuffled, the above-described experimental protocol was executed, and the area under the resulting ROC curve was recorded. The p value was computed as the occurrence frequencies of the iterations where the resulting AUCs outperformed that obtained using the original class labels. A p value <0.05 is usually considered to be statistically significant.

Figure 4:
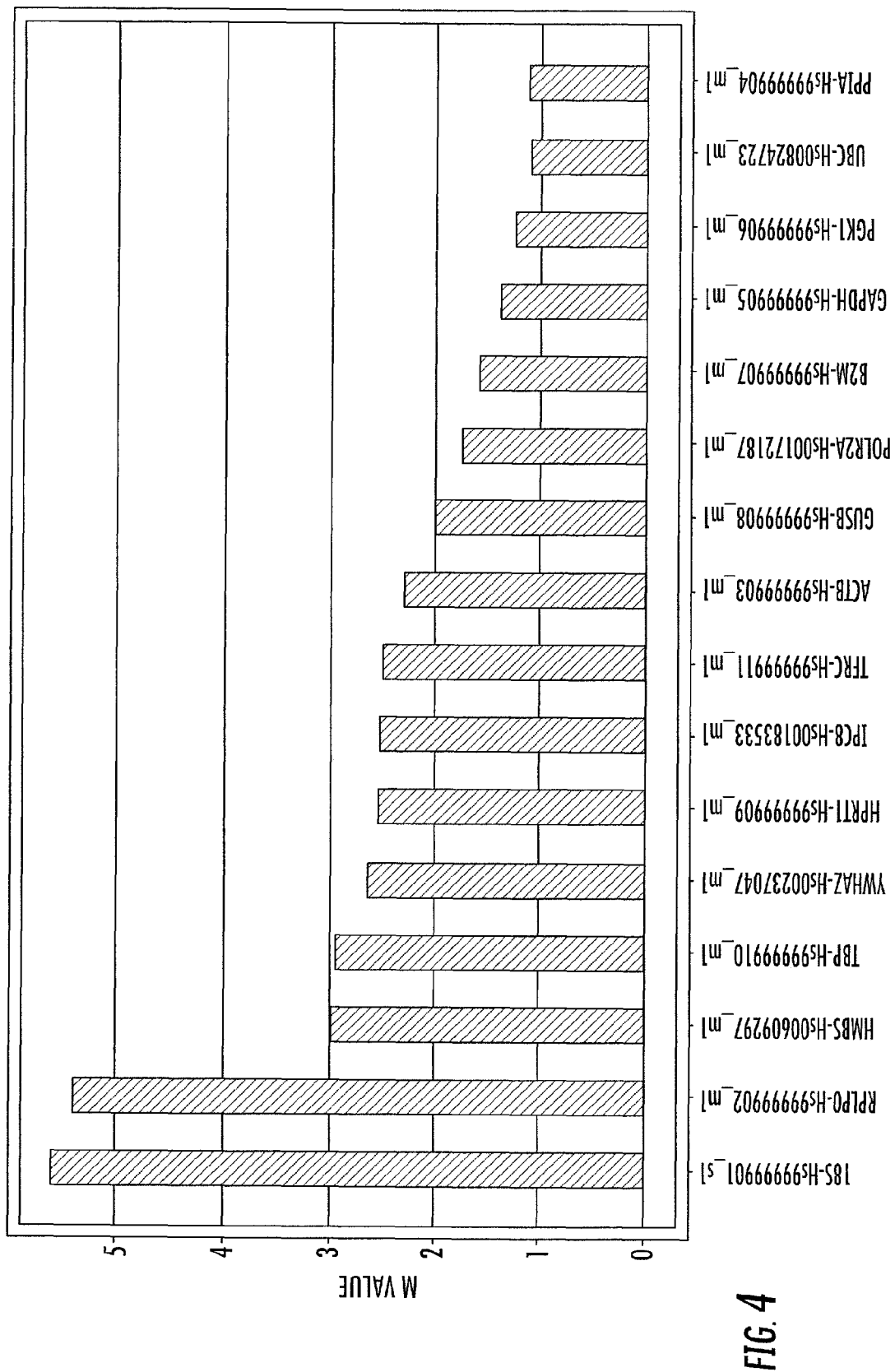
FIG. 4 is an Applied Biosystems Micro Fluidic Card TaqMan® Low Density Array (TLDA) analysis of 16 endogenous controls.

An aliquot (4 μl of total 20-μl sample) of cDNA from 81 samples in the validation cohort was preamplified and analyzed on an Applied Biosystems microfluidic card (Applied Biosystems PN 4367563). GeNorm was used to estimate the pairwise variation (standard deviation of the logarithmically transformed expression ratio) of a control gene with all the other control genes of the experiment. From this a gene stability measure, M, is calculated as the average pairwise variation. Genes with the lowest M values have the most stable expression. FIG. 4 shows that the endogenous controls UBC; PPIA; PGK1; and GAPDH were the least variable genes in the validation sample set. These 4 targets were incorporated into a 48-target custom TLDA.

In another case-control study we examined voided urines from 127 patients: 64 tumor bearing subjects, 63 controls. The urine concentrations of the following proteins were assessed by enzyme-linked immunosorbent assay (ELISA): Chemokine C-C motif ligand 18 (CCL18, also known as MIP-4); Plasminogen Activator Inhibitor 1 (PAI-1); Cluster of differentiation 44 (CD44); Vascular endothelial growth factor (VEGF); Carbonic anhydrase IX (CA9); Matrix metallopeptidase 9 (MMP9); Interleukin-8 (IL-8); Syndecan-1 (SDC1); and Angiogenin (ANG). Complete identification details are presented in Table 7.

The association (p-values) between each biomarker and BCa was tested using the Wilcoxon rank sum test. Nonparametric receiver operating characteristic (ROC) curves in which the value for sensitivity is plotted against false-positive rate (1-specificity) were generated in order to visualize and compare quantitative data. The area under the ROC curve (AUC) values and cutoffs that maximized the sum of sensitivity and specificity were calculated for comparison. Table 9 lists the AUC, cut-off value, sensitivity, specificity, positive predictive value (PPV), negative predictive value (NPV) and overall accuracy (average of the sensitivity and the specificity) for each biomarker with respect to the detection of BCa in the 127 sample cohort. Statistical significance in this study was set at p<0.05 and all reported p values were 2-sided. All analyses were performed with SAS software version 9.1.3. All data were normalized to urinary creatinine values to allow for urine volume and time in bladder. Data from analyses performed with a commercial ELISA-based BCa detection assay (BTA-Trak©) are included in Tables 8 and 9 for comparison.

TABLE 7

Complete ID of study protein markers

| Full Gene Name | Gene ID | Gene Symbol | Full Protein Name | Protein ID |
|---|---|---|---|---|
| interleukin 8 | 3576 | IL8 | Interleukin-8 | P10145 |
| matrix metallopeptidase 9 | 4318 | MMP9 | Matrix metalloproteinase-9 | P14780 |
| syndecan 1 | 6382 | SDC1 | Syndecan-1 | P18827 |
| chemokine (C-C motif) ligand 18 (pulmonary and activation-regulated) | 6362 | CCL18 | C-C motif chemokine 18 | P55774 |
| serpin peptidase inhibitor, clade E (nexin, plasminogen activator inhibitor type 1), member 1 | 5054 | PAI-1/ SERPINE1 | Plasminogen activator inhibitor 1 | P05121 |
| CD44 molecule (Indian blood group) | 960 | CD44 | CD44 antigen | P16070 |
| vascular endothelial growth factor A | 7422 | VEGF | Vascular endothelial growth factor A | P15692 |
| carbonic anhydrase IX | 768 | CA9 | Carbonic anhydrase 9 | Q16790 |
| angiogenin, ribonuclease, RNase A family, 5 | 283 | ANG | Angiogenin | P03950 |
| complement factor H-related 1-5 | 3078; 3080; 10878; 10877; 81494 | BTA | Bladder Tumor Antigen (BTA) Complement factor H-related protein 1-5 | Q03591; P36980; Q02985; Q92496; Q9BXR6 |

Urine concentrations of VEGF, CCL18, PAI-1, ANG, CA9, IL-8, and MMP9 were significantly elevated in subjects with bladder cancer (BCa) (Table 8).

TABLE 8

Comparison of urine concentration of protein markers between Cancer and Non-Cancer groups

| Biomarker | Protein ID | Concentration Units | Median (range) in Non-Cancer group | Median (range) in Cancer group |
|---|---|---|---|---|
| IL8 | P10145 | pg/ml | 0 (0-134.33) | 128.43 (0-17140.2) |
| MMP9 | P14780 | ng/ml | 0 (0-14.25) | 0.95 (0-1002.8) |
| SDC1 | P18827 | ng/ml | 40.67 (0-199.55) | 31.81 (0-335.18) |
| CCL18 | P55774 | pg/ml | 4.81 (0-37.69) | 637.39 (0-9523.04) |
| PAI-1 | P05121 | ng/ml | 0.06 (0-0.64) | 6.82 (0-125.26) |
| CD44 | P16070 | ng/ml | 117.22 (16.08-616.3) | 28.73 (16.67-344.04) |
| VEGF-A | P15692 | pg/ml | 0 (0-904.76) | 335.34 (0-9841.4) |
| CA9 | Q16790 | pg/ml | 0 (0-28.28) | 10.36 (0-4132.9) |
| ANG | P03950 | pg/ml | 44.58 (20.48-696.18) | 410.98 (3.28-17944) |
| BTA | | U/ml | 12.55 (0.5-36.87) | 179.34 (0-24865.4) |

TABLE 9

Biomarker performance data for each biomarker

| Biomarker | Protein ID | AUC | Cutoff Value | Sensitivity % | Specificity % | PPV % | NPV % | Overall Accuracy % |
|---|---|---|---|---|---|---|---|---|
| IL8 | P10145 | 0.780 | 0.272 | 59 | 95 | 93 | 70 | 78 |
| MMP9 | P14780 | 0.750 | 0.030 | 54 | 97 | 94 | 68 | 76 |
| SDC1 | P18827 | 0.610 | 1.010 | 31 | 94 | 83 | 57 | 63 |
| CCL18 | P55774 | 0.919 | 0.184 | 88 | 86 | 86 | 87 | 92 |
| PAI-1 | P05121 | 0.686 | 0.016 | 42 | 100 | 100 | 63 | 69 |
| CD44 | P16070 | 0.488 | 0.966 | 41 | 78 | 68 | 56 | 49 |
| VEGF | P15692 | 0.886 | 0.638 | 83 | 87 | 87 | 83 | 89 |
| CA9 | Q16790 | 0.732 | 0.204 | 58 | 90 | 86 | 68 | 73 |
| ANG | P03950 | 0.857 | 0.214 | 67 | 97 | 96 | 74 | 86 |
| BTA | | 0.819 | 0.318 | 80 | 84 | 84 | 80 | 82 |

To assess the independent association between biomarkers and BCa, logistic regression analysis was performed with BCa status (yes vs. no) as the response variable, and protein biomarker concentrations as the explanatory variables. A backward elimination model was used to calculate the performance parameters for all combinations (Table 10).

TABLE 10

Performance of biomarker panels by multivariate analysis Data from ELISA analysis of urine obtained from a cohort of 127 subjects.

Using all 9 biomarkers

| | | Observed | | Totals | | |
|---|---|---|---|---|---|---|
| | | Cancer | Normal | | | |
| Predicted | Cancer | 62 | 0 | 62 | 100.0% | PPV |
| | Normal | 2 | 63 | 65 | 96.9% | NPV |
| Total | | 64 | 63 | 127 | | |
| AUC | 0.9972 | (0.9920, 1.0000) | | | | |

Sensitivity 96.9%
Specificity 100.0%

3 biomarkers: CCL18, CD44 and VEGF

| | | Observed | | Totals | | |
|---|---|---|---|---|---|---|
| | | Cancer | Normal | | | |
| Predicted | Cancer | 58 | 1 | 59 | 98.3% | PPV |
| | Normal | 6 | 62 | 68 | 91.2% | NPV |
| Total | | 64 | 63 | 127 | | |
| AUC | 0.9859 | (0.9720, 0.9998) | | | | |

Sensitivity 90.6%
Specificity 98.4%

2 biomarkers: Combined biomarkers of CCL18 and VEGF

| | | Observed | | Totals | | |
|---|---|---|---|---|---|---|
| | | Cancer | Normal | | | |
| Predicted | Cancer | 62 | 9 | 71 | 87.3% | PPV |
| | Normal | 2 | 54 | 56 | 96.4% | NPV |
| Total | | 64 | 63 | 127 | | |
| AUC | 0.9616 | (0.9306, 0.9926) | | | | |

Sensitivity 96.9%
Specificity 85.7%

The performance of the full 9-biomarker assay in combination was highly accurate (Table 10a). Of the 64 cancer cases, only 2 were mislabeled (97% sensitivity), and all non-cancer cases were called correctly (100% specificity). We also calculated the performance of multiple combinations incorporating fewer biomarkers. A 3-biomarker assay (CCL18, CD44 and VEGF) performed remarkably well (sensitivity 90.6%, specificity 98.4%) (Table 10b). Reducing to 2 biomarkers (CCL18 and VEGF) (Table 10c) still outperformed (97% sensitivity, 86% specificity) currently available diagnostic tests, including BTA-Trak included in our study (80% sensitivity, 84% specificity).

One aspect of the present invention concerns materials and methods for detecting and diagnosing bladder cancer and other urogenital-related cancers. The nucleic acid molecules (e.g., DNA or mRNA) or polypeptides encoded by the nucleotides listed in Tables 2-9 can be used as molecular markers for bladder cancer.

Cancer biomarkers (also called tumor biomarkers) are molecules such as hormones, enzymes, and immunoglobulins found in the body that are associated with cancer and whose measurement or identification is useful in patient diagnosis or clinical management. They can be products of the cancer cells themselves, or of the body in response to cancer or other conditions. Most cancer biomarkers are proteins. Some cancer biomarkers are seen only in a single type of cancer, while others can be detected in several types of cancer. As with other cancer biomarkers, the biomarkers described herein can be used for a variety of purposes, such as: screening a healthy population or a high-risk population for the presence of bladder cancer; making a diagnosis of bladder cancer or of a specific type of bladder cancer; determining the prognosis of a subject; and monitoring the course in a subject in remission or while receiving surgery, radiation, chemotherapy, or other cancer treatment. Thus, urinary levels of these biomarkers can be used to detect and/or monitor the presence of bladder cancer throughout the course of disease and can be used in predicting therapeutic and prognostic outcome. For example, the biomarkers of the invention can be used to help corroborate the efficacy of chemopreventive drugs administered to treat, prevent, or delay recurrence of the disease.

One aspect of the invention concerns a method for detecting or diagnosing bladder cancer or other urogenital-related cancer in a subject, comprising detecting the presence of and/or quantifying the level of at least one biomarker listed in Tables 2-9 in a sample, such as a urine sample, from the subject, wherein the presence of the biomarker, or a level (e.g., concentration) of the biomarker above a predetermined threshold is indicative of bladder cancer or other urogenital cancer in the subject.

Figure 5:
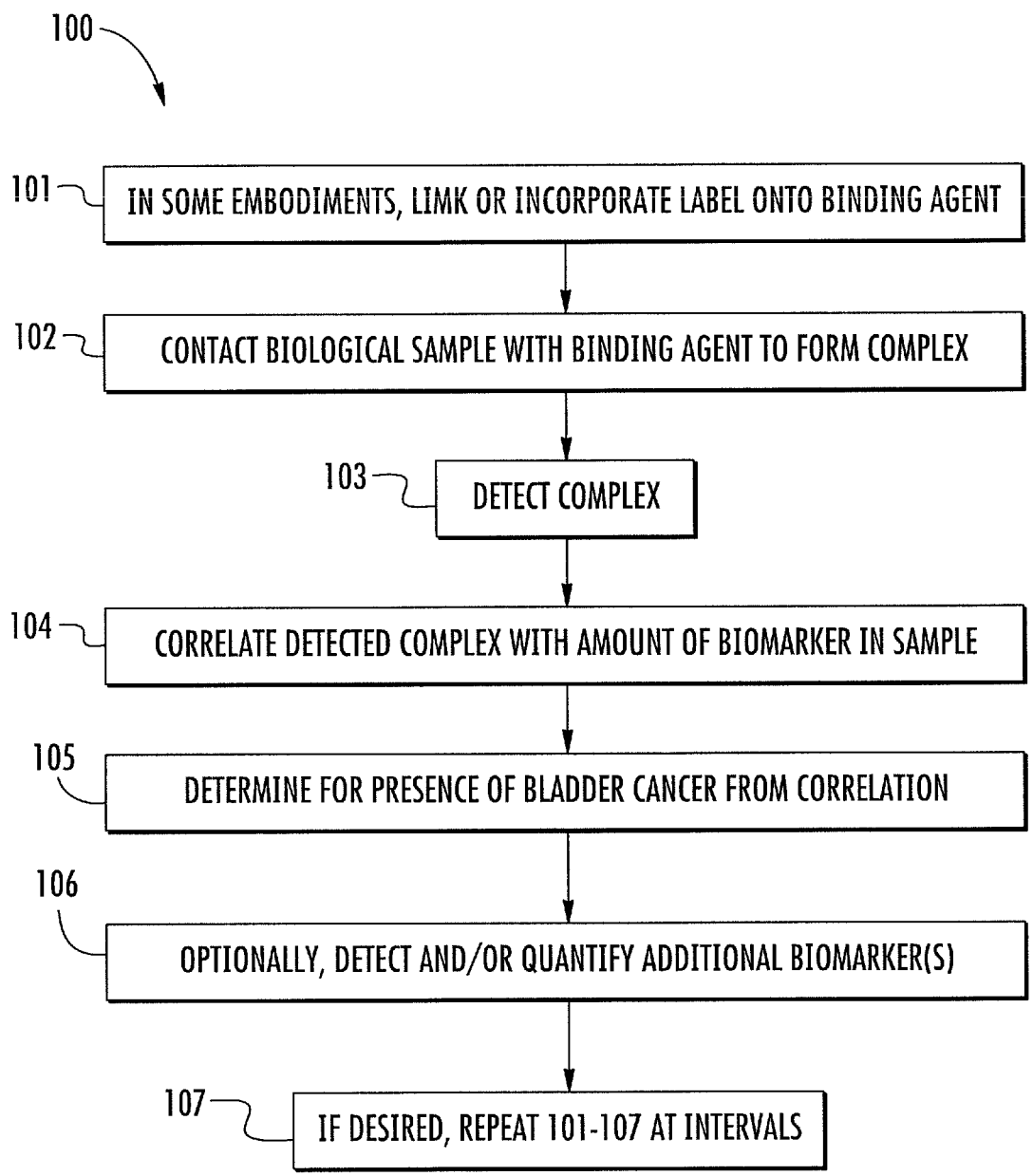
FIG. 5 is a flowchart of an embodiment of a bladder cancer detection method.

In one embodiment of a method 100 (FIG. 5) of the invention, the detecting comprises: (a) contacting a biological sample with a binding agent (or binding agents) that binds the biomarker nucleic acid or protein (or combinations of biomarkers) to form a complex (or complexes) (block 102); (b) detecting the complex(es) (block 103); and (c) correlating the detected complex(es) to the amount of biomarker in the sample (block 104), wherein the presence of one or more biomarkers, or the presence of elevated levels of biomarker(s), is indicative of bladder cancer (block 105). In a specific embodiment, the binding agent for detecting of step (b) further comprises a label linked or incorporated onto the agent (block 101). In one embodiment, the detecting comprising using ELISA-based immunoenzymatic detection.

Optionally, the methods of the invention further comprise detecting and/or quantifying one or more additional biomarkers of bladder cancer or other urogenital cancer and/or one or more additional biomarkers of a different cancer type in the same urine sample, a different urine sample, or a same or different biological sample (e.g., serum, plasma, whole blood, tissue (e.g., biopsy), exfoliated urothelial cells or bladder cancer cells) obtained from the same subject, before, during, or after said detecting of the biomarker(s) of the invention is carried out on the sample (block 106). In this way, one or more biomarkers of the invention can be used as part of a panel of biomarkers utilized in surveillance protocols for detecting bladder cancer or other urogenital cancer and, optionally, other cancers. For example, a panel of as few as 2, 3, 4, 5, 6, 7, 8, 9, 10, 11, 12, 13, or as many as 14 or more, markers could be utilized.

In some embodiments, the detecting is performed at several time points or intervals, as part of monitoring of the subject before, during, or after treatment of the cancer (block 107).

Optionally, the methods of the invention further comprise comparing the level of one or more bladder cancer biomarkers in a urine or other biological sample with the level of biomarker present in a normal control sample, wherein a higher level of biomarker in the sample as compared to the level in the normal control sample is indicative of the presence of cancer.

In some embodiments, the subject may exhibit no symptoms of cancer at the time the detecting of the bladder cancer biomarker(s) is carried out. In other embodiments, the subject exhibits one or more symptoms of cancer, such as bladder cancer, at the time the detecting of bladder cancer biomarker(s) is carried out. For example, with respect to bladder cancer, the one or more symptoms of bladder cancer can include, but are not limited to, visible blood in the urine, hematuria (the presence of microscopic red blood cells in the urine), painful urination, urgency (frequently feeling the need to urinate without results), frequent urination, and pelvic or flank pain.

Figure 6:
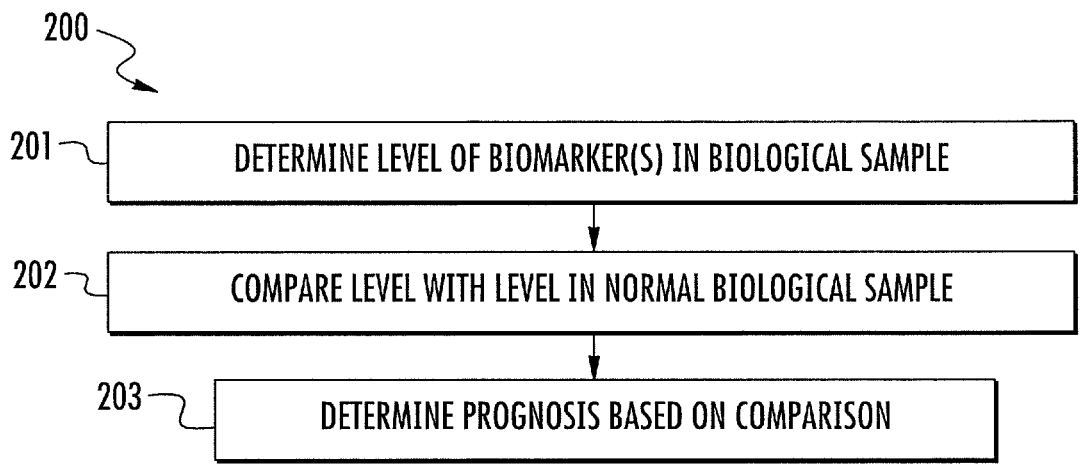
FIG. 6 is a flowchart for a method of determining a prognosis for a patient.

The subject invention also concerns methods 200 (FIG. 6) for prognostic evaluation of a subject having, or suspected of having, cancer such as bladder cancer, comprising: (a) determining the level of one or more cancer biomarkers of the present invention (block 201) (for example, one of the biomarkers listed in Tables 2-9 in a biological sample obtained from the subject; (b) comparing the level determined in step (a) to a level or range of the one or more cancer biomarkers known to be present in a biological sample obtained from a normal subject that does not have cancer (block 202); and (c) determining the prognosis of the subject based on the comparison of step (b) (block 203), wherein a high level of the one or more cancer biomarkers in step (a) indicates a more aggressive form of cancer and, therefore, a poor prognosis. In one embodiment, the biomarker comprises one or more nucleotides or polypeptides encoded by such nucleic acids, selected from Tables 2-9.

The terms "detecting" or "detect" include assaying or otherwise establishing the presence or absence of the target bladder cancer biomarker, subunits thereof, or combinations of agent bound targets, and the like, or assaying for, interrogating, ascertaining, establishing, or otherwise determining one or more factual characteristics of bladder cancer, metastasis, stage, or similar conditions. The term encompasses, but is not intended to be limited to, diagnostic, prognostic, and monitoring applications for one or more of the bladder cancer biomarkers in Tables 2-9, and, optionally, other cancer biomarkers. The term can encompass quantitative, semi-quantitative, and qualitative detection methodologies.

Nucleic Acid Assays

Nucleic acids, including naturally occurring nucleic acids, oligonucleotides, antisense oligonucleotides, and synthetic oligonucleotides that hybridize to the nucleic acid encoding biomarker polypeptides of the invention, are useful as agents to detect the presence of biomarkers of the invention in the biological samples of cancer patients or those at risk of cancer, preferably in the urine of bladder cancer patients or those at risk of bladder cancer. The present invention contemplates the use of nucleic acid sequences corresponding to the coding sequence of biomarkers of the invention and to the complementary sequence thereof, as well as sequences complementary to the biomarker transcript sequences occurring further upstream or downstream from the coding sequence (e.g., sequences contained in, or extending into, the 5' and 3' untranslated regions) for use as agents for detecting the expression of biomarkers of the invention in biological samples of cancer patients, or those at risk of cancer, preferably in the urine of bladder cancer patients or those at risk of bladder cancer.

The preferred oligonucleotides for detecting the presence of biomarkers of the invention in biological samples are those that are complementary to at least part of the cDNA sequence encoding the biomarker. These complementary sequences are also known in the art as "antisense" sequences. These oligonucleotides may be oligoribonucleotides or oligodeoxyribonucleotides. In addition, oligonucleotides may be natural oligomers composed of the biologically significant nucleotides, i.e., A (adenine), dA (deoxyadenine), G (guanine), dG (deoxyguanine), C (cytosine), dC (deoxycytosine), T (thymine), and U (uracil), or modified oligonucleotide species, substituting, for example, a methyl group or a sulfur atom for a phosphate oxygen in the inter-nucleotide phosphodiester linkage. Additionally, these nucleotides themselves, and/or the ribose moieties, may be modified.

The oligonucleotides may be synthesized chemically, using any of the known chemical oligonucleotide synthesis methods known in the art. For example, the oligonucleotides can be prepared by using any of the commercially available, automated nucleic acid synthesizers. Alternatively, the oligonucleotides may be created by standard recombinant DNA techniques, for example, inducing transcription of the noncoding strand. The DNA sequence encoding the biomarker may be inverted in a recombinant DNA system, e.g., inserted in reverse orientation downstream of a suitable promoter, such that the noncoding strand now is transcribed.

Although any length oligonucleotide may be utilized to hybridize to a nucleic acid encoding a biomarker polypeptide, oligonucleotides typically within the range of 8-100 nucleotides are preferred. Most preferable oligonucleotides for use in detecting biomarkers in urine samples are those within the range of 15-50 nucleotides.

The oligonucleotide selected for hybridizing to the biomarker nucleic acid molecule, whether synthesized chemically or by recombinant DNA technology, is then isolated and purified using standard techniques and then preferably labeled (e.g., with 35S or 32P) using standard labeling protocols.

The present invention also contemplates the use of oligonucleotide pairs in polymerase chain reactions (PCR) to detect the expression of the biomarker in biological samples. The oligonucleotide pairs include a forward primer and a reverse primer.

The presence of biomarkers in a sample from a patient may be determined by nucleic acid hybridization, such as, but not limited to, Northern blot analysis, dot blotting, Southern blot analysis, fluorescence in situ hybridization (FISH), and PCR. Chromatography, preferably HPLC, and other known assays may also be used to determine messenger RNA levels of biomarkers in a sample.

Nucleic acid molecules encoding a biomarker of the present invention can be found in the biological fluids inside a biomarker-positive cancer cell that is being shed or released in a fluid or biological sample under investigation, e.g., urine. Nucleic acids encoding biomarkers can also be found directly (i.e., cell-free) in the fluid or biological sample.

In one aspect, the present invention contemplates the use of nucleic acids as agents for detecting biomarkers of the invention in biological samples of patients, wherein the nucleic acids are labeled. The nucleic agents may be labeled with a radioactive label, a fluorescent label, an enzyme, a chemiluminescent tag, a colorimetric tag or other labels or tags that are discussed above or that are known in the art.

Protein Binding Assays

In embodiments of the invention involving detection of one or more polypeptides (as opposed to nucleic acid molecules encoding the polypeptides), the detection method may be, for example, an ELISA-based method. As used herein, the term "ELISA" includes an enzyme-linked immunoabsorbent assay that employs an antibody or antigen bound to a solid phase and an enzyme-antigen or enzyme-antibody conjugate to detect and quantify the amount of an antigen (e.g., biomarker of the invention) or antibody present in a sample. A description of the ELISA technique is found in Chapter 22 of the 4th Edition of *Basic and Clinical Immunology* by D. P. Sites et al., 1982, published by Lange Medical Publications of Los Altos, Calif., and in U.S. Pat. Nos. 3,654,090; 3,850,752; and 4,016,043, the disclosures of which are incorporated herein by reference. ELISA is an assay that can be used to quantify the amount of antigen, proteins, or other molecules of interest in a sample.

Preferably, in the various embodiments of the invention, the detection method provides an output (i.e., readout or signal) with information concerning the presence, absence, or amount of the bladder cancer biomarker(s) in a urine sample from a subject. For example, the output may be qualitative (e.g., "positive" or "negative"), or quantitative (e.g., a concentration such as nanograms per milliliter).

Figure 7:
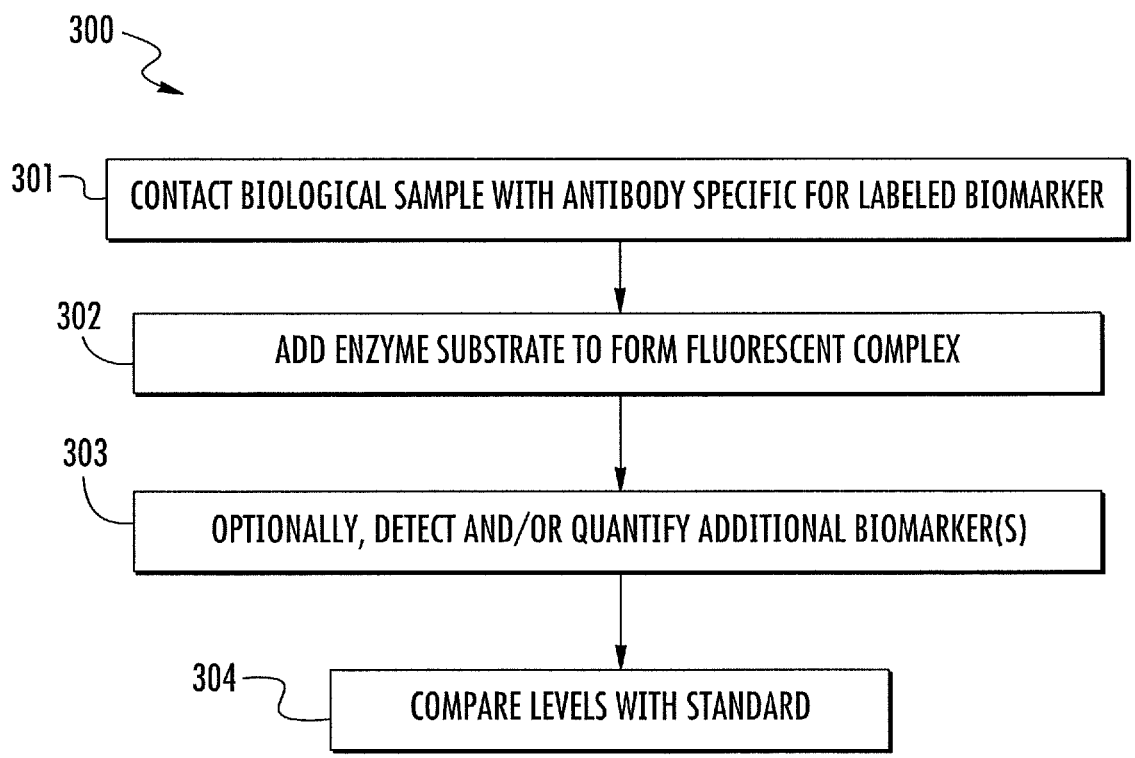
FIG. 7 is a flowchart for a method of cancer detection.

Some embodiments of the methods 300 (FIG. 7) of the invention involve (a) contacting a biological sample, such as a urine sample, from a subject with an antibody or antibodies specific for the biomarker or biomarker polypeptides that are directly or indirectly labeled with an enzyme (block 301); (b) adding a substrate for the enzyme wherein the substrate is selected so that the substrate, or a reaction product of the enzyme and substrate, forms fluorescent complexes (block 302); (c) quantifying the biomarker(s) in the sample by measuring fluorescence of the fluorescent complexes (block 303); and (d) comparing the quantified levels to that of a standard (block 304). In one embodiment, the biomarker comprises one or more polypeptides, and/or nucleic acids encoding the polypeptides, selected from one or more of biomarkers listed in Tables 2-9.

The invention also contemplates using the methods, devices, and kits described herein in conjunction with one or more additional biomarkers for cancer. The one or more additional markers may be detected before, during, and/or after detection of the one or more bladder cancer biomarkers of the invention is carried out. The methods, devices, and kits described herein may be modified by including agents to detect the additional markers, or nucleic acids encoding the markers. The methods, devices, and kits of the invention can be used for the detection of either an over-abundance or an under-abundance of one or more bladder cancer biomarkers relative to a non-disorder state or the presence of a modified (e.g., less than full length) bladder cancer biomarker that correlates with a disorder state (e.g., bladder cancer), or a progression toward a disorder state. The methods described herein can also be used to evaluate the probability of the presence of malignant or pre-malignant cells. Such methods can be used to detect tumors, quantify their growth, and assist in the diagnosis and prognosis of urogenital cancer such as bladder cancer. The methods can also be used to detect the presence of cancer metastasis, as well as confirm the absence or removal of all tumor tissue following surgery, cancer chemotherapy, and/or radiation therapy. They can further be used to monitor cancer chemotherapy and tumor reappearance.

The methods, devices, and kits of the invention can be used in the diagnosis of early-stage bladder cancer (e.g., when the subject is asymptomatic) and for monitoring and evaluating the prognosis of bladder cancer disease progression and mortality. Depending upon the particular bladder cancer biomarker of the invention, increased levels or decreased levels of detected biomarker in a urine sample compared to a standard (e.g., levels for normal or benign disorders) may be indicative of advanced disease stage, large residual tumor, and/or increased risk of disease progression and mortality.

The terms "sample," "biological sample," and the like refer to a type of material known to or suspected of expressing or containing a biomarker of cancer, such as urine. The test sample can be used directly as obtained from the source or following a pretreatment to modify the character of the sample. The sample can be derived from any biological source, such as tissues or extracts, including cells (e.g., tumor cells) and physiological fluids, such as, for example, whole blood, plasma, serum, peritoneal fluid, ascites, and the like. The sample can be obtained from animals, preferably mammals, most preferably humans. The sample can be pretreated by any method and/or can be prepared in any convenient medium that does not interfere with the assay. The sample can be treated prior to use, such as preparing plasma from blood, diluting viscous fluids, applying one or more protease inhibitors to samples such as urine, and the like. Sample treatment can involve filtration, distillation, extraction, concentration, inactivation of interfering components, the addition of reagents, and the like.

The bladder cancer biomarkers of the invention include all homologs, naturally occurring allelic variants, isoforms and precursors of the human or non-human molecules. In general, naturally occurring allelic variants of human biomarkers will share significant sequence homology (70-90%) to other sequences. Allelic variants may contain conservative amino acid substitutions or can contain a substitution of an amino acid from a corresponding position in a homologue.

The terms "subject" and "patient" are used interchangeably herein to refer to a warm-blooded animal, such as a mammal, which may be afflicted with cancer such as bladder cancer. The subject may be male or female. The term includes dogs, cats, and horses. The term also includes primates such as apes, chimps, monkeys, and humans.

Agents that are capable of detecting bladder cancer biomarkers of the invention in the urine samples of subjects are those that interact or bind with the nucleic acid or polypeptide molecule encoded by the nucleic acid. Examples of such agents (also referred to herein as binding agents) include, but are not limited to, antibodies or fragments thereof that bind the polypeptide, polypeptide binding partners, and nucleic acid molecules that hybridize to the nucleic acid molecules encoding the polypeptides. Preferably, the binding agent is labeled with a detectable substance (e.g., a detectable moiety). The binding agent may itself function as a label.

The present invention also contemplates the detection of biomarker antibodies. Thus, detection of antibodies to the biomarkers of the invention in urine of a subject may enable the diagnosis of bladder cancer and is also contemplated within the scope of the invention.

Antibodies specifically reactive with the biomarkers listed in Tables 2-9 or their derivatives, such as enzyme conjugates or labeled derivatives, may be used to the detect biomarkers in various biological samples. For example they may be used in any known immunoassays that rely on the binding interaction between an antigenic determinant of a protein and the antibodies. Examples of such assays are radioimmunoassays, enzyme immunoassay (e.g., ELISA), immunofluorescence, immunoprecipitation, latex agglutination, hemagglutination, and histochemical tests.

An antibody specific for a biomarker of the invention can be labeled with a detectable substance and localized in biological samples such as urine based upon the presence of the detectable substance. Examples of detectable substances include, but are not limited to, the following radioisotopes (e.g., $^{3}H$, $^{14}C$, $^{35}S$, $^{125}I$, $^{131}I$), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin, e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). Indirect methods may also be employed in which the primary antigen-antibody reaction is amplified by the introduction of a second antibody having specificity for the antibody reactive against the biomarker. By way of example, if the antibody having specificity against a biomarker is a rabbit IgG antibody, the second antibody may be goat anti-rabbit gamma-globulin labeled with a detectable substance.

Although the invention has been described relative to various selected embodiments herein presented by way of example, there are numerous variations and modifications that will be readily apparent to those skilled in the art in light of the above teachings. It is therefore to be understood that, within the scope of the claims hereto attached and supported by this specification, the invention may be practiced other than as specifically described.

That which is claimed is:

1. A method comprising:
   obtaining a urine sample from a subject;
   contacting the urine sample with a panel of antibodies, wherein said panel consists of antibodies that bind to and form a complex with each of the proteins in the group consisting of Interleukin-8 (IL8), Angiogenin (ANG), Plasminogen activator inhibitor 1 (PAI1), Matrix metallopeptidase 10 (MMP10) and Apolipoprotein E (APOE); and, optionally further comprises antibodies that bind to and form a complex with each of the proteins in the group consisting of selected from Carbonic anhydrase IX (CA9), Syndecan-1 (SDC1), Matrix metallopeptidase 9 (MM9) and Vascular endothelial growth factor A(VEGFA)
   detecting the presence and quantity of the protein-antibody complexes that form in the biological sample.

2. The method according to claim 1, wherein the subject was previously diagnosed with bladder cancer.

3. The method according to claim 1, wherein the sample is obtained from a subject who has had one or more symptoms of bladder cancer.

4. The method according to claim 2, wherein the urine sample has blood in it.

* * * * *

UNITED STATES PATENT AND TRADEMARK OFFICE
CERTIFICATE OF CORRECTION

PATENT NO. : 9,249,467 B2
APPLICATION NO. : 13/617878
DATED : February 2, 2016
INVENTOR(S) : Steven Goodison and Charles J. Rosser It is certified that error appears in the above-identified patent and that said Letters Patent is hereby corrected as shown below:

Specification

Column 17,
Line 28, "Using all 9" should read --Table 10a. Using all 9--.

Column 17,
Line 39, "3biomarkers" should read --Table 10b. 3biomarkers--.

Column 17,
Line 48, "2biomarkers" should read --Table 10c. 2biomarkers--.

Signed and Sealed this
Twenty-sixth Day of July, 2016

Michelle K. Lee
*Director of the United States Patent and Trademark Office*